United States Patent
Tsai et al.

(10) Patent No.: US 6,211,106 B1
(45) Date of Patent: Apr. 3, 2001

(54) GROUPS IIA AND IIIA BASED CATALYST COMPOSITION FOR PREPARING HIGH-SYNDIOTACTICITY POLYSTYRENE

(75) Inventors: Jing-Cherng Tsai; Yi-Chun Chen; Sheng Te Yang, all of Hsinchu; Meei-Hwa Wang, Chu-Nan; Shian-Jy Wang, Hsinchu, all of (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/099,911

(22) Filed: Jun. 18, 1998

(51) Int. Cl.$^7$ ................. C08F 4/44; C08F 4/52; C08F 4/76
(52) U.S. Cl. ............ 502/125; 502/118; 502/129; 502/132; 502/133; 502/154; 502/152; 526/148; 526/151; 526/160; 526/124.2; 526/346
(58) Field of Search ................. 502/118, 132, 502/154, 114, 115, 116, 125, 126, 129, 133; 526/148, 151, 162, 346, 124.2, 124.7, 125.3

(56) References Cited

U.S. PATENT DOCUMENTS

| 3,376,331 | * | 4/1968 | Kroll | 260/448 |
| 5,510,434 | * | 4/1996 | Takeuchi | 526/152 |

FOREIGN PATENT DOCUMENTS 50-142687 * 11/1975 (JP).
96/13531 * 5/1996 (WO).

* cited by examiner

Primary Examiner—David W. Wu
Assistant Examiner—R. Rabago
(74) Attorney, Agent, or Firm—W. Wayne Liauh

(57) ABSTRACT

A catalyst composition for preparing high-syndiotacticity polystyrene polymers which comprises: (a) a titanium complex represented by the following formula of $TiR'_1R'_2R'_3R'_4$ or $TiR'_1R'_2R'_3$, wherein $R'_1$, $R'_2$, $R'_3$, and $R'_4$ are, independently, an alkyl group, an aryl group, an alkoxy group, an aryloxy group, an amino group, a hydrogen atom, or a halogen atom; (b) a cyclopentadienyl complex represented by the following formula:

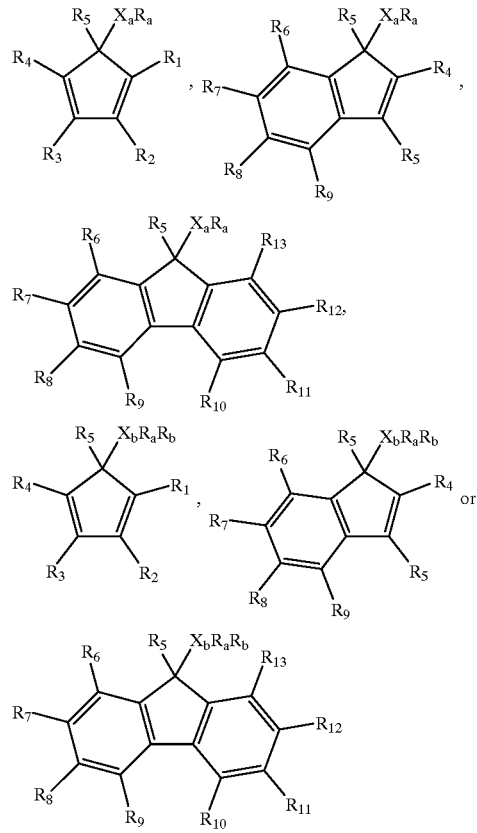

wherein $R_1$–$R_{13}$ are, independently, alkyl group, aryl group, silyl group, halogen atom, or hydrogen atom; $R_a$ and $R_b$ are, independently, alkyl group, aryl group, alkoxy, aryloxy group, cyclopentadienyl group, hydrogen atom, or halogen atom; and $X_a$ is a Group IIA element and $X_b$ is a Group IIIA element.

10 Claims, 1 Drawing Sheet

GROUPS IIA AND IIIA BASED CATALYST COMPOSITION FOR PREPARING HIGH-SYNDIOTACTICITY POLYSTYRENE

FIELD OF THE INVENTION

The present invention relates to an improved catalyst composition for preparing high-syndiotacticity polystyrene polymers. More specifically, the present invention relates to Groups IIA- and IIIA-metal based catalyst compositions for preparing polystyrene polymers which provides high activity and high syndiotacticity, and with a lowered cost.

BACKGROUND OF THE INVENTION

Peroxide is the most commonly used catalyst in the polymerization of polystyrene which causes free radicals to be generated to initiate the polymerization reaction. The polystyrene produced from the peroxide-catalyzed processes belongs to the type of atactic polystyrene (aps), which, by definition, does not possess any stereo regularity. The atactic polystyrene, which has been widely used in many commercial applications for more half century, is an amorphous polymer. The amorphous physical characteristics of atactic polystyrene have limited the range of their applications. The atactic polystyrene is primarily used in a relatively low-value added market, and they typically cannot be used in engineering plastics applications.

Isotactic polystyrene (ips), on the other hand, was also developed in as early as 1955, by G. Natta using the co-called Ziegler-Natta catalyst. The isotactic polystyrene are a highly crystalline polymer, and it exhibits a very high melting point (240° C.). These properties make the isotactic polystyrene a suitable candidate for many engineering plastics applications. However, the isotactic polystyrene suffers from the problem of having undesirably low crystallization rate, thus causing fabrication difficulties. Unless this problem can be overcome, the isotactic polystyrene does not appear to have very high commercial potential.

Relative to atactic polystyrene and isotactic polystyrene, the syndiotactic polystyrene was relatively late comer. It was not until 1986 when the syndiotactic polystyrene was first developed by Ishihara using a metallocene catalyst composition. Typically, the polymerization of syndiotactic polystyrene requires a catalyst composition containing a transitional metal titanium complex and methyl aluminoxane (or "MAO"). The concerted actions of the titanium complex and the methyl aluminoxane allows syndiotactic polystyrene to be polymerized. Descriptions of the processes for preparing syndiotactic polystyrene have been provided in, for example, European Patent Application EP 210,615, in which a catalyst composition containing tetra(ethyoxy)titanium and methyl aluminoxane was used for preparing syndiotactic polystyrene; and in world patent application WO 8,810,275, in which high syndiotacticity polystyrene was reported to have been prepared using a catalyst composition containing cyclopentadienyl trichlorotitanium and methyl aluminoxane.

U.S. Pat. Nos. 4,774,301 and 4,808,680 disclosed the use of a catalyst composition containing a transitional metal zirconium complex and methyl aluminoxane for preparing syndiotactic polystyrene. Compared to the catalyst compositions using a titanium complex and methyl aluminoxane, these catalyst compositionscontaining the zirconium complex exhibited noticeably lower activity, and the polystyrene so produced exhibited relatively lower molecular weight and lower degree of syndiotacticity.

All of the catalyst compositions described above for preparing syndiotactic polystyrene contain Group IV transitional metal complexes and methyl aluminoxane to provide activation. It should be noted that a very high excess of methyl aluminoxane is required to provide the desired activated catalyst. Because of the high cost of methyl aluminoxane, these processes have very limited commercial applications. Thus it is highly desirable to develop a metallocene based catalyst composition which can minimize, or even eliminate, the amount of methyl aluminoxane required. European Patent Application 505,890 and World Patent Application WO 930,367 disclosed a catalyst composition, which contains cyclopentadienyl trialkyl titanium as a catalyst, a non-coordinated Lewis acid as a co-catalyst, and triisobutyl aluminum as a scavenger, for the preparation of high syndiotactic polystyrene. These catalyst compositions, however, have relatively low activity.

Within the family of titanium complexes, or more specifically titanocenes, the catalytic activity, for polymerizing polystyrene, is higher for titanocenes containing one cyclopentadienyl ligand than those titanocenes containing two cyclopentadienyl ligands. The catalytic activity of the titanocene containing one cyclopentadienyl ligand is also higher than titanium complexes containing no cyclopentadienyl ligand (which is thus by definition not a titanocene). This relative relationship has been disclosed in European Patent Application EP 210,615. While the catalytic activity of the titanium complexes containing no cyclopentadienyl ligand is substantially lower than the titanocene containing one cyclopentadienyl ligand, it has the advantage of being substantially cheaper. Therefore, from economic considerations, it is highly desirable to develop a co-catalyst composition that can substantially increase the activity of the cheapest titanium complexes, that is, the titanium complexes that contain no cyclopentadienyl ligand, so as to lower the overall cost of the metallocene catalyst composition while providing excellent catalytic activity.

U.S. Pat. Nos. 5,644,009 and 5,914,375 disclose a catalyst composition for preparing high-syndiotacticity polystyrene polymers which comprises: a titanium complex and a cyclopentadienyl complex of group IV metals such as silicon (Si), germanium (Ge), or tin (Sn). Excellent catalytic activities of up to $8.1 \times 10^4$ g sPS/g Ti·hr were observed with their catalysts.

SUMMARY OF THE INVENTION

The primary object of the present invention is to develop a further improved catalyst composition for preparing high-syndiotacticity polystyrene polymers. More specifically, the primary object of the present invention is to develop an improved catalyst composition for preparing polystyrene polymers which allows the use of more economic ingredients and minimizes the expensive components such as methyl aluminoxane, so as to substantially lower cost of the catalyst composition, while providing high catalytic activity and high syndiotacticity.

Unexpected superior results, in terms of substantially higher catalytic activities, were observed by the co-inventors of the present invention when Groups IIA and IIIA metals were used in place of the Group IV metal in the cyclopentadienyl complex as disclosed in U.S. Pat. Nos. 5,644,009 and 5,914,375. An improvement in catalytic activity of more than 430% can be achieved using the catalytic composition of the present invention, compared to the Group IV based catalysts disclosed in U.S. Pat. Nos. 5,644,009 and 5,914,375. Thus, substantially economic benefits can be realized using the new catalytic composition of the present invention.

The catalyst composition disclosed in the present invention comprises the following three main components:

(a) 0.1 to 10 parts by mole a titanium complex represented by the following formula:

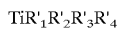

wherein $R'_1$, $R'_2$, $R'_3$, $R'_4$ can be, independently, an alkyl group, an aryl group, an alkoxy group, an aryloxy group, an amino group, or any halogen atom;

(b) 0.1 to 10 parts by mole a cyclopentadienyl complex of a Group IIA or Group IIIA metal represented by one of the following formulas:

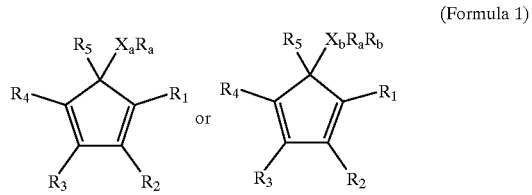

(Formula 1)

wherein $R_5$ can be alkyl group, aryl group, silyl group, hydrogen atom, or halogen atom; $R_1$ and $R_2$ can be, independently, alkyl group, aryl group, silyl group, hydrogen atom, halogen atom, or representing a benzene ring, $R_3$, and $R_4$ can be, independently, alkyl group, aryl group, silyl group, hydrogen atom, halogen atom, or representing a benzene ring; $R_a$ and $R_b$ can be, independently, alkyl group, aryl group, alkoxy, aryloxy group, cyclopentadienyl group (i.e., a radical as shown in Formula 1 without $X_aR_a$ or $X_bR_aR_b$), hydrogen atom, or halogen atom; and $X_a$ is a Group IIA element and $X_b$ is a Group IIIA element.

Examples of the cyclopentadienyl complex include: $CpAlMe_2$, $(Cp)_3B$, $CpAlClR_a$, $CpAlR_aR_b$,

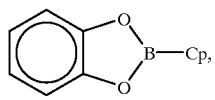

$(Cp)_2Mg$, $(Cp)_2Ba$, $CpMgR_a$, $CpBaR_a$ etc. Cp indicates a cyclopentadienyl group (again., a cyclopentadienyl radical is defined as a radical shown in Formula 1 without $X_aR_a$ or $X_bR_aR_b$). As indicated in these examples, $R_a$ and $R_b$ can be, collectively, part of a ring structure.

(c) an activated transitional metal co-catalyst: this activated transitional metal co-catalyst can be methyl aluminoxane (1 to 10,000 parts by mole), 0.1 to 20 parts by mole of a non-coordinated Lewis acid (preferably a borate, such as N,N-dimethyl anilinium tetrakis (pentafluorophenyl) borate, triphenyl carbenium tetrakis(pentafluorophenyl) borate, and ferrocenium tetrakis(pentafluorophenyl) borate), 1 to 10,000 parts by mole of a trialkyl aluminum such as triethyl aluminum or tetraisobutyl aluminum, or a mixture thereof.

Preferably the catalyst composition disclosed in the present invention contains:

(a) 0.5 to 2 parts by mole of the titanium (IV) or titanium (III) complex;

(b) 1 to 4 parts by mole of the cyclopentadienyl complex of the Group IIA or IIIA element; and (c) 10 to 1,000 parts by mole of the methyl aluminoxane, or a mixture containing 0.5 to 4 parts by mole of the non-coordinated Lewis acid and 0 to 1,000 parts by mole of the trialkyl aluminum.

Also preferably, the Group IIA or IIIA element is aluminum, barium, magnesium, or boron, and the cyclopentadienyl complex is dimethyl(pentamethylcyclopentadienyl) aluminum, B-(pentamethylcyclopentadienyl) catecholborane, Bis(pentamethylcyclopentadienyl) magnesium, or Bis(n-propyltetramethylcyclopentadienyl) barium.

If the activated transitional metal co-catalyst contains the mixture of non-coordinated Lewis acid and trialkyl aluminum, the preferred amount of the cyclopentadienyl complex is from 0.5 to 2 parts by mole.

When $R_1$ and $R_2$ collectively represent a benzene ring, then the cyclopentadienyl complex of the present invention is represented by one of the following formulas:

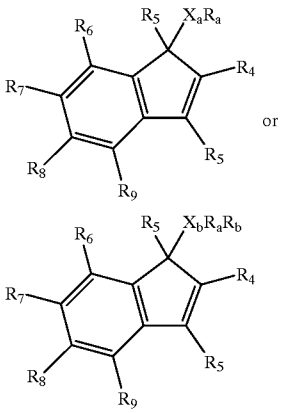

Wherein $R_6$, $R_7$, $R_8$, and $R_9$ can be alkyl group, aryl group, silyl group, hydrogen atom, or halogen atom.

When both pairs of $R_1$ and $R_2$ and $R_3$ and $R_4$ collectively represent a benzene ring, then the cyclopentadienyl complex of the present invention is represented by one of the following formulas:

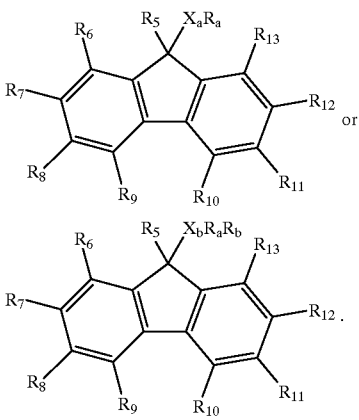

Wherein $R_6$, $R_7$, $R_8$, $R_9$, $R_{10}$, $R_{11}$, $R_{12}$, and $R_{13}$ can be alkyl group, aryl group, silyl group, hydrogen atom, or halogen atom.

In the improved catalyst composition disclosed in the present invention, the titanium complex can be a Ti(III) complex, instead of the Ti(IV) complex as described in (a), above. In this embodiment, the titanium complex is represented, rather, by the formula of $TiR'_1R'_2R'_3$, wherein $R'_1$, $R'_2$, $R'_3$, can be, independently, an alkyl group, an aryl group, an alkoxy group, an aryloxy group, an amino group, or a halogen element.

One of the advantages of the catalyst composition disclosed in the present invention is that it causes a very inexpensive chemical, i.e., either $TiR'_1R'_2R'_3R'_4$ or $TiR'_1R'_2R'_3$, to exhibit high activity in the production of high-syndiotacticity polystyrene polymers from styrene or other aryl ethylene monomers. $TiR'_1R'_2R'_3R'_4$ and $TiR'_1R'_2R'_3$ have largely been considered as having only low activity in making syndiotactic polystyrene. With the present invention, the cost of the catalyst can be substantially reduced, compared to the conventional catalysts of similar activity and syndiotacticity. Another advantage of the catalyst composition disclosed in the present invention is that it is not very sensitive to degradation by exposure to air and moisture. Most catalysts for the preparation of syndiotactic polystyrene contain cyclopendadiene-coordinated titanium, such as cyclopentadienyl trichlorotitanium and cyclopentadienyl trimethoxytitanium, whose activities are known to be sensitive to air and moisture. The present invention, thus, discloses an improved catalyst composition for the preparation of high-syndiotacticity polystyrene which exhibits superior activities and stability on storage, and can be made at a substantially lowered cost.

BRIEF DESCRIPTION OF THE DRAWING

The present invention will be described in detail with reference to the drawing showing the preferred embodiment of the present invention, wherein.

DETAILED DESCRIPTION OF THE PREFERRED EMBODIMENT

Figure 1:
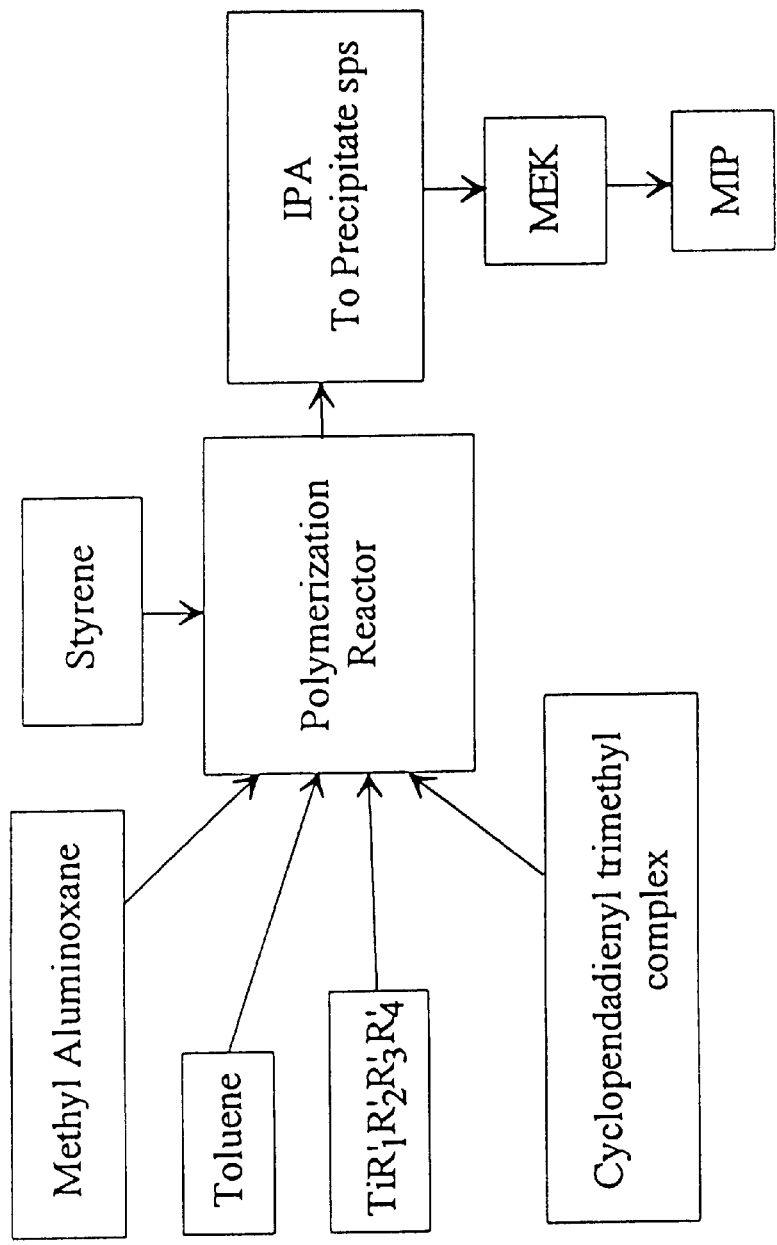
FIG. 1 is a flow chart diagram showing the steps of a preferred embodiment of the process disclosed in the present invention utilizing an improved catalyst composition for the preparation of high-syndiotacticity polystyrene polymers.

The present invention discloses a novel Group IIA or Group IIIA based catalyst composition for preparing high-syndiotacticity polystyrene polymers, and the process of utilizing this high-activity catalyst composition. The improved catalyst composition disclosed in the present invention allows the use of a very economical ingredient thus substantially lowering the manufacturing cost of the catalyst composition, while providing high activity and high syndiotacticity comparable to the best commercial products at substantially higher cost.

The catalyst composition disclosed in the present invention comprises the following three main components:

(a) 0.1 to 10 parts by mole of a a titanium complex represented by the following formula:

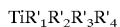

wherein $R'_1$, $R'_2$, $R'_3$, and $R'_4$ are, independently, an alkyl group, an aryl group, an alkoxy group, an aryloxy group, an amino group, or a halogen atom.

In the improved catalyst composition disclosed in the present invention, the titanium complex can be a Ti(III) complex, instead of the Ti(IV) complex as described in (a), above. In this embodiment, the titanium complex is represented, rather, by the formula of $TiR'_1R'_2R'_3$, wherein $R'_1$, $R'_2$, $R'_3$, can be, independently, an alkyl group, an aryl group, an alkoxy group, an aryloxy group, an amino group, or a halogen atom.

(b) 0.1 to 10 parts by mole of a cyclopentadienyl complex of a Group IIA or Group IIIA element represented by one of the following formulas:

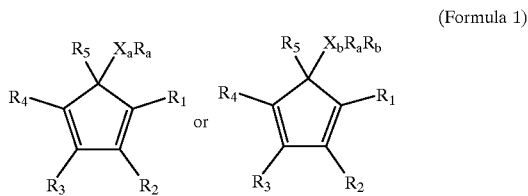

(Formula 1)

wherein $R_5$ can be alkyl group, aryl group, silyl group, germanyl group, stannyl group, hydrogen atom, or halogen atom; $R_1$ and $R_2$ can be, independently, alkyl group, aryl group, silyl group, germanyl group, stannyl group, hydrogen atom, halogen atom, or part of a benzene ring; $R_3$, and $R_4$ can be, independently, alkyl group, aryl group, silyl group, hydrogen atom, halogen atom, or part of a benzene ring; $R_a$ and $R_b$ can be, independently, alkyl group, aryl group, alkoxy, aryloxy group, cyclopentadienyl group (i.e., a radical as shown in Formula 1 without $X_aR_a$ or $X_bR_aR_b$), hydrogen atom, or halogen atom; and $X_a$ is a Group IIA element and $X_b$ is a Group IIIA element. Examples of the cyclopentadienyl complex include: $CpAlMe_2$, $(Cp)_3B$, $CpAlClR_a$, $CpAlR_aR_b$,

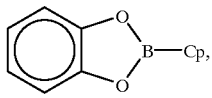

$(Cp)_2Mg$, $(Cp)_2Ba$, $CpMgR_a$, $CpBaR_a$ etc. Cp indicates a cyclopentadienyl group (again, a cyclopentadienyl radical is defined as a radical shown in Formula 1 without $XR_a$ or $XR_aR_b$). In other words, Cp can be expressed as $C_5(R)_5$, wherein $(R)_5$, which can be the same of different from each other, represent of $R_1$ through $R_5$. As indicated in these examples, $R_a$ and $R_b$ can be, collectively, part of a ring structure.

(c) an activated transitional metal co-catalyst.

When $R_1$ and $R_2$ collectively represent a benzene ring, then the cyclopentadienyl complex of the present invention is represented by one of the following formulas:

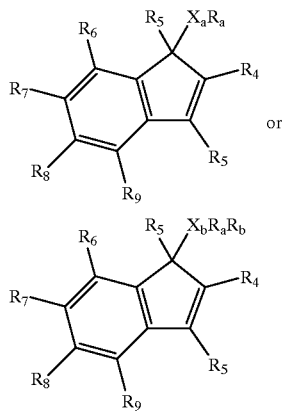

Wherein $R_6$, $R_7$, $R_8$, and $R_9$ can be alkyl group, aryl group, silyl group, hydrogen atom, or halogen atom.

When both pairs of ($R_1$ and $R_2$) and ($R_3$ and $R_4$) collectively and respectively represent a benzene ring, then the cyclopentadienyl complex of the present invention is represented by one of the following formulas:

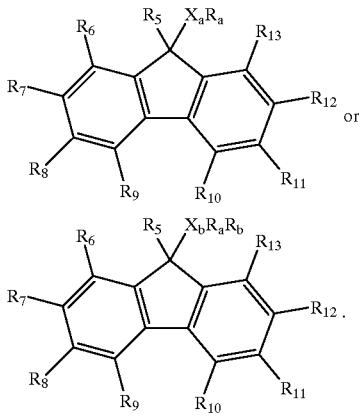

Wherein $R_6$, $R_7$, $R_8$, $R_9$, $R_{10}$, $R_{11}$, $R_{12}$, and $R_{13}$ can be alkyl group, aryl group, silyl group, hydrogen atom, or halogen atom.

Preferably, the Group IIA or IIIA element is aluminum, barium, magnesium, or boron, and the cyclopentadienyl complex is dimethyl(pentamethylcyclopentadienyl) aluminum, B-(pentamethylcyclopentadienyl) catecholborane, Bis(pentamethylcyclopentadienyl) magnesium, or Bis(n-propyltetramethylcyclopentadienyl) barium.

This activated transitional metal co-catalyst can be methyl aluminoxane (1 to 10,000 parts by mole), 0.1 to 20 parts by mole of a non-coordinated Lewis acid (a Lewis acid is an electron-pair donor), 1 to 10,000 parts by mole of a trialkyl aluminum, such as triethyl aluminum or tetraisobutyl aluminum, or a mixture thereof. Preferably the non-coordinated Lewis acid is a borate such as N,N-dimethyl anilinium tetrakis (pentafluorophenyl) borate, triphenyl carbenium tetrakis(pentafluorophenyl) borate, and ferrocenium tetrakis(pentafluorophenyl) borate.

As discussed above, one of the advantages of the catalyst composition disclosed in the present invention is that it can utilize a very inexpensive chemical (compared to titanocenes), i.e., either $TiR'_1R'_2R'_3R'_4$ or $TiR'_1R'_2R'_3$, as an important ingredient to provide high activity catalytic function in the production of high-syndiotacticity polystyrene polymers from styrene or other aryl ethylene monomers. The titanium complexes $TiR'_1R'_2R'_3R'_4$ and $TiR'_1R'_2R'_3$ have been considered as an ineffective catalyst ingredient in the polymerization of syndiotactic polystyrene because of their relatively poor activity. With the present invention, because it can utilize these inexpensive ingredients while providing comparable or even superior results, the cost of the required catalyst can be reduced by almost one order of magnitude, compared to the conventional catalysts of similar activity and syndiotacticity. Furthermore, most of these catalysts for the preparation of syndiotactic polystyrene contain cyclopendadiene-coordinated titanium (i.e., titanocenes), such as cyclopentadienyl trichlorotitanium and cyclopentadienyl trimethoxytitanium, which have been known to be highly sensitive to environmental variables such as air and moisture. Another advantage of the catalyst composition disclosed in the present invention is that it is not very sensitive to degradation by exposure to air and/or moisture. The present invention, thus, discloses an improved catalyst composition for the preparation of high-syndiotacticity polystyrene which exhibits superior activities and stability on storage, and can be made at a substantially lowered cost.

FIG. 1 is a flow chart diagram showing the steps of a preferred embodiment of the process disclosed in the present invention. A polystyrene reactor maintained at 50° C. is first charged with nitrogen gas to purge air. 110 ml of toluene and an appropriate amount of methyl aluminoxane are added into the reactor, followed by the addition of the Group IIA or IIIA based cyclopentadienyl complex and a titanium (IV) complex, $TiR'_1R'_2R'_3R'_4$. The reaction mixture is stirred for 5 minutes, then styrene monomers are added to start the polymerization reaction. After about one hour, when the polymerization reaction is complete, the reaction mixture (which contains the reaction product) is quenched with IPA to isolate syndiotactic polystyrene (sps) by precipitation. The syndiotactic polystyrene so obtained is extracted with MEK to remove amorphous polystyrene. The insoluble portion is conventionally called the MIP (MEK-insoluble portion), which is an indication of the ratio between syndiotactic polystyrene and atactic polystyrene.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1

1.14 g of lithium pentamethylcyclopentadiene ($C_5Me_5Li$) and 50 ml of toluene were added into a 100-ml Schlenk flask bottle at room temperature. Then 8 ml of dimethylaluminum chloride (1M in hexane) was added to the mixture. The mixture solution was heated at 80° C. for four hours. After the removal of LiCl, the filtrate was vacuum dried to obtain a yellowish dimethyl(pentamethylcyclopentadienyl) aluminum. The yield was 78%.

The dimethyl(pentamethylcyclopentadienyl)aluminum so prepared was mixed with titanium (IV) n-butoxide in a 1:1 molar ratio. This formed the catalyst composition of Example 1.

EXAMPLE 2

1.0 g of lithium pentamethylcyclopentadiene and 40 ml of toluene were added into a 100-ml Schlenk flask bottle at room temperature. Then 1.08 g of B-chlorocatecholborane in 10 ml of toluene was gradually added to the mixture at a temperature of 0° C. The solution mixture was stirred overnight at room temperature. After the removal of LiCl, the filtrate was vacuum dried to obtain a yellowish B-pentamethylcyclopentadienylcatecholborane. The yield was 83%.

The B-pentamethylcyclopentadienylcatecholborane so prepared was mixed with titanium (IV) n-butoxide in a 1:1 molar ratio. This formed the catalyst composition of Example 2.

EXAMPLE 3

Bis(pentamethylcyclopentadienyl)magnesium was prepared in a procedure similar to those described above. The Bis(pentamethylcyclopentadienyl)magnesium so prepared was mixed with titanium (IV) n-butoxide in a 1:2 molar ratio. This formed the catalyst composition of Example 3.

EXAMPLE 4

Bis(n-propyltetramethylcyclopentadienyl)barium was prepared in a procedure similar to those described above.

The Bis(n-propyltetramethylcyclopentadienyl)barium so prepared was mixed with titanium (IV) n-butoxide in a 1:2 molar ratio. This formed the catalyst composition of Example 4.

EXAMPLE 5

A one-liter sPS reactor was purged with nitrogen for half an hour. Then 300 ml of styrene which had been purified with $Al_2O_3$ was charged into the sPS reactor. The temperature of the reactor was raised to 70° C., and 1 ml of 22 wt % triisobutylaluminum was added to the reactor followed by 1.5 ml of 1.49 M MAO. Finally, $8\times10^{-6}$ mole of catalyst composition of Example 1 was added. The reactor was maintained at a hydrogen pressure of 0.2 Kg. The reaction was stopped after half an hour. After filtration and drying (at 80° C. and under a reduced pressure), 91 g of syndiotactic polystyrene were obtained. This represented a catalytic activity of $4.75\times10^5$ g sPS/g Ti·hr. A solvent extraction procedure was applied to measure the aPS/sPS ratio using methyl ethyl ketone. The MEK-insoluble portion (MIP) was measured to be 98.5%

EXAMPLE 6

A one-liter sPS reactor was purged with nitrogen for half an hour. Then 300 ml of styrene which had been purified with $Al_2O_3$ was charged into the sPS reactor. The temperature of the reactor was raised to 70° C., and 1 ml of 22 wt % triisobutylaluminum was added to the reactor followed by 1.5 ml of 1.49 M MAO. Finally, $1.5\times10^{-5}$ mole of catalyst composition of Example 3 was added. The reactor was maintained at a hydrogen pressure of 0.2 Kg. The reaction was stopped after half an hour. After filtration and drying (at 80° C. and under a reduced pressure), 106.6 g of syndiotactic polystyrene were obtained. This represented a catalytic activity of $2.96\times10^5$ g sPS/g Ti·hr.

EXAMPLE 7

A one-liter sPS reactor was purged with nitrogen for half an hour. Then 300 ml of styrene which had been purified with $Al_2O_3$ was charged into the sPS reactor. The temperature of the reactor was raised to 70° C., and 1 ml of 22 wt % triisobutylaluminum was added to the reactor followed by 1.5 ml of 1.49 M MAO. Finally, $7.5\times10^{-6}$ mole of catalyst composition of Example 3 and $1.5\times10^{-5}$ mole of trimethylsilyl chloride were added. The reactor was maintained at a hydrogen pressure of 0.2 Kg. The reaction was stopped after half an hour. After filtration and drying (at 80° C. and under a reduced pressure), 68.9 g of syndiotactic polystyrene were obtained. This represented a catalytic activity of $3.82\times10^5$ g sPS/g Ti·hr.

EXAMPLE 8

A one-liter sPS reactor was purged with nitrogen for half an hour. Then 300 ml of styrene which had been purified with $Al_2O_3$ was charged into the sPS reactor. The temperature of the reactor was raised to 70° C., and 2 ml of 22 wt % triisobutylaluminum was added to the reactor followed by 3.0 ml of 1.49 M MAO. Finally, $1.5\times10^{-5}$ mole of catalyst composition of Example 4 was added. The reactor was maintained at a hydrogen pressure of 0.2 Kg. The reaction was stopped after half an hour. After filtration and drying (at 80° C. and under a reduced pressure), 66 g of syndiotactic polystyrene were obtained. This represented a catalytic activity of $3.68\times10^5$ g sPS/g Ti·hr.

EXAMPLE 9

A one-liter sPS reactor was purged with nitrogen for half an hour. Then 300 ml of styrene which had been purified with $Al_2O_3$ was charged into the sPS reactor. The temperature of the reactor was raised to 70° C., and 0.4 ml of 22 wt % triisobutylaluminum was added to the reactor followed by 0.9 ml of 1.49 M MAO. Finally, $1.7\times10^{-5}$ mole of catalyst composition of Example 1 was added. The reactor was maintained at a hydrogen pressure of 0.2 Kg. The reaction was stopped after half an hour. After filtration and drying (at 80° C. and under a reduced pressure), 99 g of syndiotactic polystyrene were obtained. This represented a catalytic activity of $2.42\times10^5$ g sPS/g Ti·hr.

EXAMPLE 10

A one-liter sPS reactor was purged with nitrogen for half an hour. Then 300 ml of styrene which had been purified with $Al_2O_3$ was charged into the sPS reactor. The temperature of the reactor was raised to 70° C., and 2.0 ml of 22 wt % triisobutylaluminum was added to the reactor followed by 3.0 ml of 1.49 M MAO. Finally, $3\times10^{-5}$ mole of catalyst composition of Example 2 was added. The reactor was maintained at a hydrogen pressure of 0.2 Kg. The reaction was stopped after half an hour. After filtration and drying (at 80° C. and under a reduced pressure), 13 g of syndiotactic polystyrene were obtained. This represented a catalytic activity of $9.0\times10^3$ g sPS/g Ti·hr.

Comparative Example A1

100 ml of toluene was added into a 450-ml Fisher-Porter bottle, which was equipped with an electrically powered stirrer. The reaction bottle was heated until its internal temperature reached 70° C., then methyl aluminoxane (containing 6.6 mmole Al) was added. Subsequently, 0.75 ml of $1.6\times10^{-2}$ M triisopropoxychloro titanium, $ClTi(O-iPr)_3$, in toluene, and 0.75 ml of $1.6\times10^{-2}$M tetramethylcyclopentadienyltrimethyl silicon in toluene were added. Finally 20 ml of styrene monomer was added to begin the polymerization reaction. After the reaction was continued at 70° C. for one hour, methanol was added to stop the reaction. While syndiotactic polystyrene particles were precipitated from the reaction mixture. After filtration and drying (at 80° C. and under a reduced pressure), 11.35 g of syndiotactic polystyrene were obtained. This represented a catalytic activity of $2.0\times10^4$ g sPS/g Ti·hr. The syndiotacticity of the syndiotactic polystyrene so produced was analyzed using NMR to be 98%. A Soxhlet extraction procedure was also performed to measure the aPS/sPS ratio using methylethyl ketone. The MEK-insoluble portion (MIP) was measured to be 92%.

Comparative Example B1

The procedure in Comparable Example 1 was identical to that in Example 1, except that the reaction mixture did not contain tetramethylcyclopentadienyltrimethyl silicon. In this example, the catalyst composition contained only methyl 6.6 mmole of aluminoxane (measured based on the content of Al) and 0.75 ml of $1.6\times10^{-2}$ M $ClTi(O-iPr)_3$ in toluene. After the steps of polymerization reaction, precipitation with methanol, filtration, and drying, 0.42 g of sps was obtained, representing a catalytic activity of $8.5\times10^2$ g sPS/g Ti·hr.

Comparative Example A2

100 ml of toluene was added into a 450-ml Fisher-Porter bottle, which was equipped with an electrically powered stirrer. The reaction bottle was heated until its internal temperature reached 70° C., then methyl aluminoxane (containing 6.6 mmole Al) was added. Subsequently, 0.75 ml of $1.6\times10^{-2}$ M triisopropoxychloro titanium, $ClTi(O-iPr)$ $_3$, in toluene, and 0.75 ml of $1.6 \times 10^{-2}$ M tetramethylcyclopentadienyl-tri(n-butyl) tin in toluene were added. Finally 20 ml of styrene monomer was added to begin the polymerization reaction. After the reaction was continued at 70° C. for one hour, methanol was added to stop the reaction. White syndiotactic polystyrene particles were precipitated from the reaction mixture. After filtration and drying (at 80° C. and under a reduced pressure), 3.42 g of syndiotactic polystyrene were obtained. This represented a catalytic activity of $6.0 \times 10^3$ g sPS/g Ti·hr.

Comparative Example A3

100 ml of toluene was added into a 450-ml Fisher-Porter bottle, which was equipped with an electrically powered stirrer. The reaction bottle was heated until its internal temperature reached 70° C., then a mixture containing 1.21 ml ($4.8 \times 10^{-3}$ mole) of triisobutyl aluminum (a trialkyl aluminum) and 0.012 g ($1.4 \times 10^{-5}$ mole) of N,N-dimethyl anilinium tetrakis (pentafluorophenyl) borate (a non-coordinated Lewis acid) was added. This was followed by the addition of 0.75 ml of $1.6 \times 10^{-2}$ M tetraethoxy titanium, Ti(OEt)$_4$, in toluene, and 0.75 ml of $1.6 \times 10^{-2}$ M tetramethylcyclopentadienyl-trimethyl silicon in toluene. Finally 20 ml of styrene monomer was added to begin the polymerization reaction. After the reaction was continued at 70° C. for one hour, methanol was added to stop the reaction. While syndiotactic polystyrene particles were precipitated from the reaction mixture. After filtration and drying (at 80° C. and under a reduced pressure), 7.24 g of syndiotactic polystyrene were obtained. This represented a catalytic activity of $1.3 \times 10^4$ g sPS/g Ti·hr.

Comparative Example A4

100 ml of styrene was added into a 450-ml Fisher-Porter bottle, which was equipped with an electrically powered stirrer. Then methyl aluminoxane (containing 12 mmole Al) was added. The reaction bottle was heated until its internal temperature reached 70° C. Subsequently, $2.4 \times 10^{-5}$ mole of triisopropoxychloro titanium, ClTi(O-iPr)$_3$ and $2.4 \times 10^{-5}$ mole of tetramethylcyclopentadienyltrimethyl silicon were added to begin the polymerization reaction. After the reaction was continued at 70° C. for 20 minutes, excess amounts of methanol were added to stop the reaction. White syndiotactic polystyrene particles were precipitated from the reaction mixture. After filtration and drying (at 80° C. and under a reduced pressure), 23.34 g of syndiotactic polystyrene (mp=269° C.) were obtained. This represented a catalytic activity of $6.1 \times 10^4$ g sPS/g Ti·hr.

Comparative Example A5

50 ml of styrene was added into a 450-ml Fisher-Porter bottle, which was equipped with an electrically powered stirrer. Then methyl aluminoxane (containing 12 mmole Al) was added. The reaction bottle was heated until its internal temperature reached 70° C. Subsequently, $2.4 \times 10^{-5}$ mole of triisopropoxychloro titanium, ClTi(O-iPr)$_3$ and $2.4 \times 10^{-5}$ mole of trimethyl silyl indene were added to begin the polymerization reaction. After the reaction was continued at 70° C. for 20 minutes, excess amounts of methanol were added to stop the reaction. White syndiotactic polystyrene particles were precipitated from the reaction mixture. After filtration and drying (at 80° C. and under a reduced pressure), 23.34 g of syndiotactic polystyrene (mp=268° C. and syndiotacticity>95%) were obtained. This represented a catalytic activity of $2.2 \times 10^4$ g sPS/g Ti·hr.

Comparative Example A6

500 ml of styrene was added into a 1-liter Fisher-Porter bottle, which was equipped with an electrically powered stirrer. Then methyl aluminoxane (containing 12 mmole Al) was added. The reaction bottle was heated until its internal temperature reached 70° C. Subsequently, $2.4 \times 10^{-5}$ mole of triisopropoxychloro titanium, ClTi(O-iPr)$_3$, in toluene, and $2.4 \times 10^{-5}$ mole of pentamethylcyclopentadienyl trimethyl silicon were added into the styrene solution to begin the polymerization reaction. After the reaction was continued at 70° C. for one hour, excess methanol was added to quench the reaction. White particles of sPS were collected after filtration. 92.6 g of syndiotactic polystyrene (mp=270° C.) were obtained after drying. This represented a catalytic activity of $8.1 \times 10^4$ g sPS/g Ti·hr.

Comparative Example A7

500 ml of styrene was added into a 1-liter Fisher-Porter bottle, which was equipped with an electrically powered stirrer. Then methyl aluminoxane (containing 12 mmole Al) was added. The reaction bottle was heated until its internal temperature reached 50° C. Subsequently, $2.4 \times 10^{-5}$ mole of triisopropoxychloro titanium, ClTi(O-iPr)$_3$, in toluene, and $2.4 \times 10^{-5}$ mole of cyclopentadienyl trimethyl silicon were added into the styrene solution to begin the polymerization reaction. After the reaction was continued at 50° C. for one hour, excess methanol was added to quench the reaction. White particles of sPS were collected after filtration. 10.2 g of syndiotactic polystyrene (mp=260° C.) were obtained after drying. This represented a catalytic activity of $8.9 \times 10^3$ g sPS/g Ti·hr.

Comparative Example A8

500 ml of styrene was added into a 1-liter Fisher-Porter bottle, which was equipped with an electrically powered stirrer. Then methyl aluminoxane (containing 12 mmole Al) was added. The reaction bottle was heated until its internal temperature reached 60° C. Subsequently, $2.4 \times 10^{-5}$ mole of triisopropoxychloro titanium, ClTi(O-iPr)$_3$, in toluene, and $2.4 \times 10^{-5}$ mole of trimethyl silyl indene silicon were added into the styrene solution to begin the polymerization reaction. After the reaction was continued at 60° C. for one hour, excess methanol was added to quench the reaction. White particles of sPS were collected after filtration. 18.6 g of syndiotactic polystyrene (mp=270° C.) were obtained after drying. This represented a catalytic activity of $1.6 \times 10^4$ g sPS/g Ti·hr.

Comparative Example A9

500 ml of styrene was added into a 1-liter Fisher-Porter bottle, which was equipped with an electrically powered stirrer. Then methyl aluminoxane (containing 12 mmole Al) was added. The reaction bottle was heated until its internal temperature reached 60° C. Subsequently, $2.4 \times 10^{-5}$ mole of triisopropoxychloro titanium, ClTi(O-iPr)$_3$, in toluene, and $2.4 \times 10^{-5}$ mole of tetramethylcyclopentadienyl trimethyl tin (in toluene) were added into the styrene solution to begin the polymerization reaction. After the reaction was continued at 60° C. for 30 minutes, excess methanol was added to quench the reaction. White particles of sPS were collected after filtration. 6.6 g of syndiotactic polystyrene (mp=270° C.) were obtained after drying. This represented a catalytic activity of $1.1 \times 10^4$ g sPS/g Ti·hr.

Comparative Example A10

500 ml of styrene was added into a 1-liter Fisher-Porter bottle, which was equipped with an electrically powered stirrer. Then methyl aluminoxane (containing 12 mmole Al)

was added. The reaction bottle was heated until its internal temperature reached 60° C. Subsequently, 2.4×10⁻⁵ mole of triisopropoxychloro titanium, ClTi(O-iPr)$_3$, in toluene, and 2.4×10⁻⁵ mole of trimethyl indenyl tin (in toluene) were added into the styrene solution to begin the polymerization reaction. After the reaction was continued at 60° C. for 30 minutes, excess methanol was added to quench the reaction. White particles of sPS were collected after filtration. 2.9 g of syndiotactic polystyrene (mp=270° C.) were obtained after drying. This represented a catalytic activity of 5.0×10³ g sPS/g Ti·hr.

Comparative Example A11

500 ml of styrene was added into a 1-liter Fisher-Porter bottle, which was equipped with an electrically powered stirrer. Then triisobutyl aluminum in toluene (containing 12 mmole Al) was added. The reaction bottle was heated until its internal temperature reached 70° C. Subsequently, 2.9×10⁻⁵ mole of N-N-dimethylanilinium tetrakis (pentafluorophenyl)borate, (PhNMe$_2$H⁺)[B(C$_6$F$_5$)$_4$]⁻ was added into the styrene solution, followed by the addition of 2.4×10⁻⁵ mole of tetraethoxy titanium, Ti(OEt)$_4$, in toluene, and 2.4×10⁻⁵ mole of pentamethylcyclopentadienyl trimethyl silicon, to begin the polymerization reaction. After the reaction was continued at 70° C. for one hour, excess methanol was added to quench the reaction. White particles of sPS were collected after filtration. 31.7 g of syndiotactic polystyrene (mp=270° C.) were obtained after drying. This represented a catalytic activity of 2.8×10⁴ g sPS/g Ti·hr.

Comparative Example A12

500 ml of styrene was added into a 1-liter Fisher-Porter bottle, which was equipped with an electrically powered stirrer. Then triisobutyl aluminum in toluene (containing 12 mmole Al) was added. The solution was heated until its internal temperature reached 60° C. Subsequently, 2.9×10⁻⁵ mole of N-N-dimethylanilinium tetrakis(pentafluorophenyl) borate, (PhNMe$_2$H⁺)[B(C$_6$F$_5$)$_4$]⁻ was added into the styrene solution, followed by the addition of 2.4×10⁻⁵ mole of tetraethoxy titanium, Ti(OEt)$_4$, in toluene, and 2.4×10⁻⁵ mole of tetramethylcyclopentadienyl trimethyl silicon, to begin the polymerization reaction. After the reaction was continued at 60° C. for 30 minutes, excess methanol was added to quench the reaction. White particles of sPS were collected after filtration. 8.2 g of syndiotactic polystyrene (mp=270° C.) were obtained after drying. This represented a catalytic activity of 1.4×10⁴ g sPS/g Ti·hr.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A catalyst composition for the preparation of high-syndiotacticity polystyrene or other aryl ethylene polymers from styrene or substituted styrene comprising:

(a) 0.1 to 10 parts by mole of a titanium (IV) complex represented by the following formula of TiR'$_1$R'$_2$R'$_3$R'$_4$, wherein each of said R'$_1$, R'$_2$, R'$_3$, and R'$^4$ is, independently, an alkyl group, an aryl group, an alkoxy group, an aryloxy group, an amino group, or a halogen atom;

(b) 0.1 to 10 parts by mole of a cyclopentadienyl complex of a Group IIA or Group IIIA element represented by one of the following formulas:

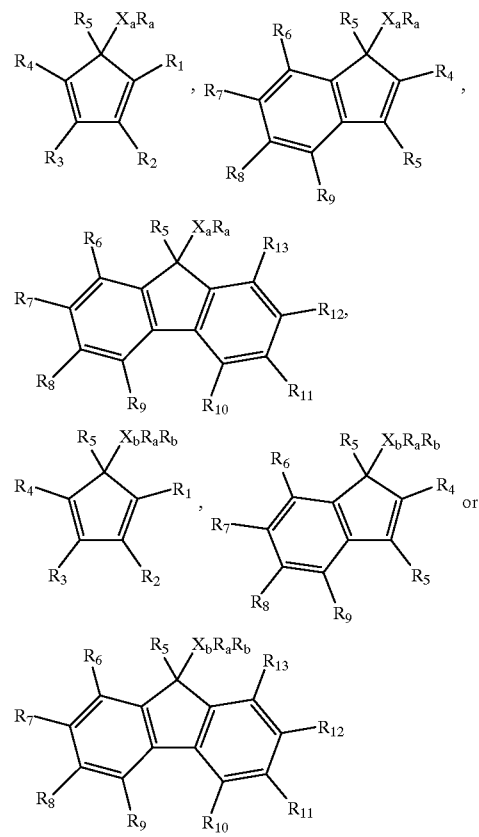

wherein R$_a$, R$_b$, and R$_{1-13}$ are independently selected from the group consisting of methyl group and hydrogen atom; and X$_a$ is a Group IIA element and X$_b$ is a Group IIIA element; and (c) an activated transitional metal co-catalyst which comprises 1 to 10,000 parts by mole of methyl aluminoxane, 0.1 to 20 parts by mole of a non-coordinated Lewis acid, 1 to 1,000 parts by mole of a trialkyl aluminum, or a mixture thereof;

(d) wherein said substituted styrene is a C$_{1-12}$-substituted styrene or a mono- or poly-halogenated styrene.

2. The catalyst composition according to claim 1 wherein X$_a$ and X$_b$ are aluminum, magnesium, boron, or barium.

3. The catalyst composition according to claim 1 wherein X$_a$ and X$_b$ are aluminum, magnesium, or barium.

4. The catalyst composition according to claim 1 wherein said cyclopentadienyl complex is represented by one of the following formulas:

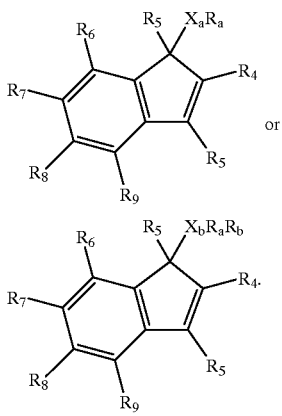

5. The catalyst composition according to claim 1 wherein said cyclopentadienyl complex is represented by one of the following formulas:

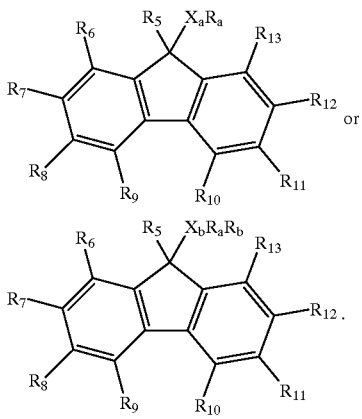

6. The catalyst composition according to claim 1 wherein each of said $R'_1$, $R'_2$, $R'_3$, and $R'_4$ is, independently, an alkyl group, an aryl group, an alkoxy group, an aryloxy group, or an amino group.

7. The catalyst composition according to claim 1 wherein each of said $R'_1$, $R'_2$, $R'_3$, $R'_4$ is an alkoxy group or an aryloxy group.

8. The catalyst composition according to claim 1 wherein each of said $R'_1$, $R'_2$, $R'_3$, and $R'_4$ is an alkoxy group.

9. A catalyst composition for the preparation of high-syndiotacticity polystyrene or other aryl ethylene polymers from styrene or substituted styrene comprising:

(a) 0.1 to 10 parts by mole a a titanium (IV) complex represented by the following formula of $TiR'_1R'_2R'_3R'_4$, wherein each of said $R'_1$, $R'_2$, $R'_3$, and $R'_4$ is, independently, an alkyl group, an aryl group, an alkoxy group, an aryloxy group, an amino group, or a halogen atom;

(b) 0.1 to 10 parts by mole of a cyclopentadienyl complex selected from the group consisting of $CpAlMe_2$, $(Cp)_3B$, $CpAlClR_a$, $CpAlR_aR_b$,

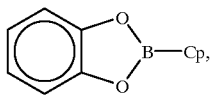

$(Cp)_2Ba$, $CpMgR_a$, and $CpBaR_a$, wherein Cp indicates a cyclopentadienyl group and $R_a$ $R_b$ are independently hydrogen or methyl; and (c) an activated transitional metal co-catalyst which comprises 1 to 10,000 parts by mole of methyl aluminoxane, 0.1 to 20 parts by mole of a non-coordinated Lewis acid, 1 to 1,000 parts by mole of a trialkyl aluminum, or a mixture thereof;

(d) wherein said substituted styrene is a $C_{1-12}$-substituted styrene or a mono- or poly-halogenated styrene.

10. A catalyst composition for the preparation of high-syndiotacticity polystyrene or other aryl ethylene polymers from styrene or substituted styrene comprising:

(a) 0.1 to 10 parts by mole of a titanium (IV) complex represented by the following formula of $TiR'_1R'_2R'_3R'_4$, wherein each of said $R'_1$, $R'_2$, $R'_3$, and $R'_4$ is, independently, an alkyl group, an aryl group, an alkoxy group, an aryloxy group, an amino group, or a halogen atom;

(b) 0.1 to 10 parts by mole of a cyclopentadienyl complex selected from the group consisting of dimethyl (pentamethylcyclopentadienyl) aluminum, B-(pentamethylcyclopentadienyl)catecholborane, Bis (pentamethylcyclopentadienyl) magnesium, and Bis(n-propyltetramethylcyclopentadienyl) barium; and (c) an activated transitional metal co-catalyst which comprises 1 to 10,000 parts by mole of methyl aluminoxane, 0.1 to 20 parts by mole of a non-coordinated Lewis acid, 1 to 1,000 parts by mole of a trialkyl aluminum, or a mixture thereof;

(d) wherein said substituted styrene is a $C_{1-12}$-substituted styrene or a mono- or poly-halogenated styrene.

* * * * *